US012653922B2

(12) United States Patent
Gajendra et al.

(10) Patent No.: US 12,653,922 B2
(45) Date of Patent: Jun. 16, 2026

(54) AIRCRAFT LAVATORY WITH INTEGRATED AIR IONIZER

(71) Applicant: B/E Aerospace, Inc., Winston-Salem, NC (US)

(72) Inventors: Hemanth Raghav Gajendra, Bangalore (IN); Sai Sankalp Shekar, Bengaluru (IN); Skandan Berikai Kuppan, Bangalore (IN)

(73) Assignee: B/E AEROSPACE, INC., Winston-Salem, NC (US)

( * ) Notice: Subject to any disclaimer, the term of this patent is extended or adjusted under 35 U.S.C. 154(b) by 100 days.

(21) Appl. No.: 18/595,108

(22) Filed: Mar. 4, 2024

(65) Prior Publication Data

US 2025/0073370 A1      Mar. 6, 2025

(30) Foreign Application Priority Data

Sep. 1, 2023    (IN) .............................. 202341058834

(51) Int. Cl.
    *A61L 9/22*      (2006.01)
    *B64D 11/02*     (2006.01)
(52) U.S. Cl.
    CPC ................ *A61L 9/22* (2013.01); *B64D 11/02* (2013.01); *A61L 2209/11* (2013.01)
(58) Field of Classification Search
    CPC ......... A61L 9/22; A61L 2209/11; B64D 11/02
    USPC ......................................................... 361/231
    See application file for complete search history.

(56) References Cited

U.S. PATENT DOCUMENTS

| | | | |
|---|---|---|---|
| 941,744 | A | 11/1909 | Tattoon |
| 4,361,014 | A | 11/1982 | Blain |
| 4,384,191 | A | 5/1983 | Guibert |
| 4,546,939 | A | 10/1985 | Cronin |
| 5,125,597 | A | 6/1992 | Coffinberry |
| 5,309,724 | A | 5/1994 | Schreiber et al. |
| 5,373,707 | A | 12/1994 | Ostersetzer et al. |
| 5,461,882 | A | 10/1995 | Zywiak |
| 5,802,863 | A | 9/1998 | Cowans |
| 6,128,909 | A | 10/2000 | Jonqueres |
| 6,658,881 | B1 | 12/2003 | Plattner |
| 6,668,563 | B2 | 12/2003 | Mirowsky et al. |
| 6,730,141 | B2 | 5/2004 | Goebel et al. |

(Continued)

FOREIGN PATENT DOCUMENTS

| | | |
|---|---|---|
| BR | 102014021726 | 12/2021 |
| BR | 102016002790 | 1/2023 |

(Continued)

OTHER PUBLICATIONS

European Patent Office, Partial European Search Report dated Jan. 29, 2025 in Application No. 24209243.5.

(Continued)

*Primary Examiner* — Sreeya Sreevatsa
(74) *Attorney, Agent, or Firm* — SNELL & WILMER L.L.P.

(57)        ABSTRACT

An aircraft lavatory is disclosed herein. The aircraft lavatory includes an air duct including an air inlet and an air outlet, the air outlet extending into an interior of the aircraft lavatory, an ion emitter coupled to the air outlet, and a control unit electronically coupled to the ion emitter, the control unit configured to control an ion output of the ion emitter.

13 Claims, 7 Drawing Sheets

(56) References Cited

U.S. PATENT DOCUMENTS

| | | | |
|---|---|---|---|
| 6,817,575 B1 | 11/2004 | Munoz et al. | |
| 6,948,331 B1 | 9/2005 | Ho | |
| 7,121,100 B2 | 10/2006 | Atkey et al. | |
| 8,171,749 B2 | 5/2012 | Lu et al. | |
| 8,607,586 B2 | 12/2013 | Lu | |
| 8,656,727 B2 | 2/2014 | Ullman et al. | |
| RE44,815 E | 3/2014 | Pierson | |
| 8,720,217 B2 | 5/2014 | Reed et al. | |
| 9,169,024 B2 | 10/2015 | Voinov | |
| 9,239,005 B2 | 1/2016 | Strecker et al. | |
| 9,284,057 B2 | 3/2016 | Kelnhofer | |
| 9,422,060 B2 | 8/2016 | Smith et al. | |
| 9,467,023 B2 | 10/2016 | Pal | |
| 9,481,468 B1 | 11/2016 | Schiff | |
| 9,487,299 B2 | 11/2016 | Oswald et al. | |
| 9,611,043 B2 | 4/2017 | Piesker | |
| 9,623,982 B2 | 4/2017 | Sharma | |
| 9,821,914 B2 | 11/2017 | Klimpel et al. | |
| 9,840,329 B2 | 12/2017 | Godecker et al. | |
| 9,914,526 B2 | 3/2018 | Reiss et al. | |
| 9,976,684 B2 | 5/2018 | Kelnhofer et al. | |
| 10,107,565 B2 | 10/2018 | Shubat et al. | |
| 10,239,618 B2 | 3/2019 | Burd | |
| 10,293,941 B2 | 5/2019 | Moran | |
| 10,358,223 B2 | 7/2019 | Dessero et al. | |
| 10,364,043 B2 | 7/2019 | Gandolfi et al. | |
| 10,399,683 B2 | 9/2019 | Behrens et al. | |
| 10,704,466 B2 | 7/2020 | Dierksmeier | |
| 10,850,856 B2 | 12/2020 | Hothi | |
| 10,914,242 B2 | 2/2021 | Staubach et al. | |
| 11,014,677 B2 | 5/2021 | DeFrancesco et al. | |
| 11,059,593 B2 | 7/2021 | Fagundes et al. | |
| 11,077,949 B2 | 8/2021 | Behrens et al. | |
| 11,136,125 B2 | 10/2021 | Tsai et al. | |
| 11,214,373 B2 | 1/2022 | Schalla et al. | |
| 11,220,340 B2 | 1/2022 | Chylinski et al. | |
| 11,231,204 B2 | 1/2022 | Burd | |
| 11,286,049 B2 | 3/2022 | Burd | |
| 11,401,703 B1 | 8/2022 | Tsai | |
| 11,485,497 B2 | 11/2022 | Lu | |
| 11,485,499 B2 | 11/2022 | Rambo | |
| 11,492,126 B2 | 11/2022 | Burd | |
| 11,492,127 B2 | 11/2022 | Retersdorf | |
| 11,572,172 B2 | 2/2023 | Burgess et al. | |
| 11,573,045 B2 | 2/2023 | Moran | |
| 11,643,213 B2 | 5/2023 | Moran | |
| 11,680,715 B1 | 6/2023 | Broach | |
| 2004/0163536 A1 | 8/2004 | Baudat et al. | |
| 2005/0063130 A1* | 3/2005 | Francis | H01T 23/00 361/220 |
| 2009/0260387 A1 | 10/2009 | DeFrancesco | |
| 2009/0277993 A1 | 11/2009 | Storch | |
| 2010/0307332 A1 | 12/2010 | Yuen | |
| 2011/0192565 A1 | 8/2011 | Markwart et al. | |
| 2014/0338383 A1 | 11/2014 | Simadiris et al. | |
| 2014/0345304 A1 | 11/2014 | Leung et al. | |
| 2015/0188171 A1 | 7/2015 | Boodaghians et al. | |
| 2016/0201983 A1 | 7/2016 | Sharma | |
| 2017/0183100 A1 | 6/2017 | Du et al. | |
| 2018/0231276 A1 | 8/2018 | Hansen et al. | |
| 2019/0352012 A1 | 11/2019 | Vue | |
| 2020/0362757 A1 | 11/2020 | Brady | |
| 2021/0070449 A1 | 3/2021 | Rogers | |
| 2021/0285697 A1 | 9/2021 | Burd | |
| 2021/0300544 A1 | 9/2021 | Scholl et al. | |
| 2021/0323682 A1 | 10/2021 | Evans et al. | |
| 2022/0053905 A1* | 2/2022 | Siu | A45D 20/12 |
| 2022/0133928 A1* | 5/2022 | Stuck | A61L 2/14 422/121 |
| 2022/0194589 A1 | 6/2022 | Hu et al. | |
| 2022/0194604 A1 | 6/2022 | Winter | |
| 2022/0332427 A1 | 10/2022 | Will et al. | |
| 2023/0061757 A1* | 3/2023 | Smithson | A61L 9/20 |

FOREIGN PATENT DOCUMENTS

| | | | |
|---|---|---|---|
| BR | 102016007170 | | 1/2023 |
| BR | 102016006921 | | 4/2023 |
| CA | 2060999 | | 4/1995 |
| CA | 2130629 | | 7/2004 |
| CA | 2416398 | | 3/2011 |
| CA | 2740081 | | 6/2018 |
| CA | 2836053 | | 1/2020 |
| CA | 2952685 | | 2/2021 |
| CA | 2922424 | | 2/2023 |
| CN | 202835618 | | 3/2013 |
| CN | 101657355 | | 4/2013 |
| CN | 105593622 | | 5/2016 |
| CN | 105526730 | | 5/2018 |
| CN | 105531185 | | 6/2018 |
| CN | 109099518 | | 12/2018 |
| CN | 106660635 | | 10/2019 |
| CN | 212213047 | | 12/2020 |
| CN | 107344621 | | 1/2021 |
| CN | 112177778 | | 1/2021 |
| CN | 112429244 | A | 3/2021 |
| CN | 113548188 | | 10/2021 |
| CN | 215260277 | | 12/2021 |
| CN | 114044146 | | 2/2022 |
| CN | 114165915 | | 3/2022 |
| CN | 114209154 | | 3/2022 |
| CN | 114408186 | | 4/2022 |
| CN | 114408188 | | 4/2022 |
| CN | 216557619 | | 5/2022 |
| CN | 108725799 | | 6/2022 |
| CN | 114486265 | | 6/2022 |
| CN | 114671029 | | 6/2022 |
| CN | 114715410 | | 7/2022 |
| CN | 108016620 | | 4/2023 |
| CN | 113716052 | | 4/2023 |
| CN | 109515723 | | 5/2023 |
| DE | 2834256 | | 5/1985 |
| DE | 3071530 | | 5/1986 |
| DE | 69105354 | | 1/1995 |
| DE | 69502501 | | 6/1998 |
| DE | 19733934 | | 7/1998 |
| DE | 19952523 | | 5/2001 |
| DE | 19952524 | | 5/2001 |
| DE | 602004005106 | | 4/2007 |
| DE | 602005003167 | | 8/2008 |
| DE | 602004012509 | | 4/2009 |
| DE | 602004012694 | | 4/2009 |
| DE | 602004012689 | | 5/2009 |
| DE | 602004012695 | | 5/2009 |
| DE | 602005005892 | | 7/2009 |
| DE | 102008062038 | | 6/2010 |
| DE | 602004030826 | | 2/2011 |
| DE | 102006041030 | | 11/2014 |
| DE | 102013008620 | | 11/2014 |
| DE | 102013211177 | | 12/2014 |
| DE | 102011014565 | | 11/2016 |
| DE | 102016125562 | | 6/2018 |
| DE | 102020003962 | | 6/2022 |
| DE | 102016222650 | | 9/2022 |
| EP | 0019492 | | 1/1982 |
| EP | 1878660 | | 11/2010 |
| EP | 2307827 | | 4/2011 |
| EP | 1790568 | | 1/2012 |
| EP | 1801009 | | 7/2013 |
| EP | 2801526 | | 11/2014 |
| EP | 1155958 | | 4/2015 |
| EP | 2888167 | | 7/2015 |
| EP | 1700068 | | 9/2015 |
| EP | 2191210 | | 11/2015 |
| EP | 2594485 | | 1/2016 |
| EP | 2319761 | | 8/2016 |
| EP | 2874880 | | 8/2016 |
| EP | 2799337 | | 11/2016 |
| EP | 1748907 | | 5/2017 |
| EP | 2710313 | | 6/2017 |
| EP | 2620727 | | 8/2017 |
| EP | 2828152 | | 8/2017 |
| EP | 2538162 | | 11/2017 |

(56) References Cited

FOREIGN PATENT DOCUMENTS

| | | |
|---|---|---|
| EP | 2889218 | 11/2018 |
| EP | 3038917 | 1/2019 |
| EP | 2499443 | 3/2019 |
| EP | 3235724 | 6/2019 |
| EP | 3038918 | 7/2019 |
| EP | 3296208 | 7/2019 |
| EP | 2851295 | 3/2020 |
| EP | 2969756 | 3/2020 |
| EP | 2386811 | 4/2020 |
| EP | 2687794 | 4/2020 |
| EP | 3123085 | 6/2020 |
| EP | 2917660 | 10/2020 |
| EP | 3130543 | 10/2020 |
| EP | 3333078 | 10/2020 |
| EP | 3055631 | 12/2020 |
| EP | 3017256 | 3/2021 |
| EP | 2828594 | 4/2021 |
| EP | 2403728 | 6/2021 |
| EP | 2836430 | 6/2021 |
| EP | 3052872 | 7/2021 |
| EP | 3878744 | 9/2021 |
| EP | 2807081 | 11/2021 |
| EP | 3539870 | 11/2021 |
| EP | 3925884 | 12/2021 |
| EP | 3639636 | 5/2022 |
| EP | 3992565 | 5/2022 |
| EP | 2830942 | 11/2022 |
| EP | 4112463 | 1/2023 |
| EP | 3708004 | 4/2023 |
| EP | 3839380 | 4/2023 |
| EP | 3885264 | 5/2023 |
| ES | 2214370 | 9/2004 |
| ES | 2271161 | 4/2007 |
| ES | 2279045 | 8/2007 |
| ES | 2372632 | 1/2012 |
| ES | 2648103 | 12/2017 |
| ES | 2715843 | 6/2019 |
| ES | 2912999 | 5/2022 |
| ES | 2913796 | 6/2022 |
| FR | 2711309 | 4/1995 |
| FR | 2894563 | 6/2007 |
| FR | 3002315 | 3/2018 |
| GB | 2413838 | 8/2007 |
| HK | 1156685 | 6/2012 |
| HK | 1166291 | 1/2022 |
| IN | 201500140 | 7/2016 |
| IN | 201502330 | 7/2016 |
| JP | 10155562 | 6/1998 |
| JP | 10332178 | 12/1998 |
| JP | 2000318695 | 11/2000 |
| JP | 2000344198 | 12/2000 |
| JP | 2001010596 | 1/2001 |
| JP | 2001071999 | 3/2001 |
| JP | 2004012087 | 1/2004 |
| JP | 2005060139 | 3/2005 |
| JP | 03915263 | 5/2007 |
| JP | 04381852 | 12/2009 |
| JP | 2011158247 | 8/2011 |
| JP | 2011168159 | 9/2011 |
| JP | 04787832 | 10/2011 |
| JP | 05336077 | 11/2013 |
| JP | 2015528889 | 10/2015 |
| JP | 05848436 | 1/2016 |
| JP | 05976396 | 8/2016 |
| JP | 06281981 | 2/2018 |
| JP | 07029256 | 3/2022 |
| KR | 20050029345 | 3/2005 |
| KR | 2011105469 | 9/2011 |
| KR | 1277502 | 6/2013 |
| KR | 1873846 | 7/2018 |
| KR | 2124120 | 6/2020 |
| KR | 2185992 | 12/2020 |
| KR | 2432143 | 8/2022 |
| KR | 2023056073 | 4/2023 |
| SG | 10201507728 | 9/2018 |
| TH | 177417 | 7/2018 |
| WO | WO2002076827 | 10/2002 |
| WO | WO2005063570 | 7/2005 |
| WO | WO2011058075 | 10/2011 |
| WO | WO2016059698 | 4/2016 |
| WO | WO2017027406 | 2/2017 |
| WO | WO2017107719 | 6/2017 |
| WO | 2022207586 | 10/2022 |
| WO | WO2022218626 | 10/2022 |

OTHER PUBLICATIONS

European Patent Office, European Search Report dated Apr. 29, 2025 in Application No. 24209243.5.

European Patent Office, European Search Report dated Jan. 29, 2025 in Application No. 24195872.7.

For references HK1166291B and HK 1166291A—corresponding application EP 2403728 is disclosed.

For reference HK1156685A—corresponding application EP 2307827 is disclosed.

For reference SG10201507728—corresponding application JP6281981B2 is disclosed.

For reference DE3071530—corresponding application EP0019492B1 is disclosed.

For reference DE69105354—corresponding US app 5125597 is disclosed.

For reference DE69502501—corresponding US app 5461882 is disclosed.

For reference DE602004030826D1—corresponding application WO2005063570 is disclosed.

For reference TH177417—corresponding application WO2016059698 is disclosed.

For reference IN20150233014—corresponding India application as filed (2330 /CHE/2015) is disclosed; corresponding US matter 20160201983.

For reference IN20150014014—corresponding India application as filed (140/CHE/2015), corresponding US matter 20160201983.

European Patent Office, European Office Action dated Mar. 20, 2026 in Application No. 24195872.7.

USPTO; Requirement for Restriction dated May 13, 2026 in U.S. Appl. No. 18/593,659.

* cited by examiner

AIRCRAFT LAVATORY WITH INTEGRATED AIR IONIZER

CROSS-REFERENCE TO RELATED APPLICATIONS

This application claims priority to, and the benefit of, India Provisional Patent Application No. 202341058834, filed Sep. 1, 2023 and titled "AIRCRAFT LAVATORY WITH INTEGRATED AIR IONIZER," which is incorporated by reference herein in its entirety for all purposes.

FIELD

The present disclosure generally relates to systems for managing air quality in an aircraft, and more specifically, to using air ionizers in an aircraft

BACKGROUND

Travel within aircraft includes the recirculation of air within the aircraft. Circulation of air within an enclosed space, such as aircraft, may include circulation of harmful pathogens (e.g., viruses, bacteria, etc.) and undesirable odors. Currently, commercial aircraft use air filters, including high efficiency particulate air (HEPA) filters, to filter the air during recirculation. Generally, air filters are placed at central locations and therefore may not have continuous effectiveness within the enclosed space. Furthermore, more effective air filters, such as HEPA filters, come with an increased cost both in terms of the filter itself as well as the energy used to force air through the air filter. Furthermore, air filters, including HEPA filters, do not remove odors from the air within the enclosed space.

SUMMARY

An aircraft lavatory is disclosed herein. The aircraft lavatory includes an air duct including an air inlet and an air outlet, the air outlet extending into an interior of the aircraft lavatory, an ion emitter coupled to the air outlet, and a control unit electronically coupled to the ion emitter, the control unit configured to control an ion output of the ion emitter.

In various embodiments, the ion emitter is configured to be in an air flow passing through the air outlet. In various embodiments, the ion emitter is perpendicular to the air flow passing through the air outlet. In various embodiments, the air outlet includes an opening having an outer circumference and the ion emitter is coupled to the opening and extends inward from the outer circumference.

In various embodiments, the aircraft lavatory further includes a plurality of ion emitters arranged around the outer circumference of the opening, wherein each of the plurality of ion emitters is perpendicular to a flow of air passing through the opening. In various embodiments, the air inlet extends to an exterior of the aircraft lavatory to provide the air duct with air from outside of the aircraft lavatory. In various embodiments, the control unit includes a voltage input having a first voltage and a voltage output having a second voltage that is greater than the first voltage, the voltage output being coupled to the ion emitter.

Also disclosed herein is an aircraft including a lavatory including an interior and an exterior, an air duct extending from the exterior of the lavatory to the interior of the lavatory, the air duct including an air outlet disposed within the interior of the lavatory, an ion emitter coupled to the air outlet, and a control unit electronically coupled to the ion emitter, the control unit configured to control an ion generation of the ion emitter.

In various embodiments, the ion emitter is configured to be in an air flow passing through the air outlet and into the interior of the lavatory. In various embodiments, the ion emitter is perpendicular to the air flow passing through the air outlet. In various embodiments, the air outlet includes an opening having an outer circumference and the ion emitter is coupled to the opening and extends inward from the outer circumference. In various embodiments, the aircraft further includes a plurality of ion emitters arranged around the outer circumference of the opening, wherein each of the plurality of ion emitters is perpendicular to a flow of air passing through the opening.

In various embodiments, the lavatory further includes an interior wall disposed between the control unit and the interior of the lavatory. In various embodiments, the control unit includes a voltage input having a first voltage and a voltage output having a second voltage that is greater than the first voltage, the voltage output being coupled to the ion emitter.

Also disclosed herein is a system including a first ion emitter coupled to a first air outlet inside a first lavatory, a first control unit electronically coupled to the first ion emitter, a graphical user interface, a processor electronically coupled to the first control unit, and a memory operatively coupled to the processor, the memory comprising instructions stored thereon that, when executed by the processor, cause the processor to receive an input from the graphical user interface and send a first signal to the first control unit to adjust a first voltage to the first ion emitter in response to the input.

In various embodiments, the system further includes a second ion emitter coupled to a second air outlet inside a second lavatory and a second control unit electronically coupled to the second ion emitter wherein the instructions, when executed by the processor, further cause the processor to send a second signal to the second control unit to adjust a second voltage of the second ion emitter in response to the input. In various embodiments, the instructions, when executed by the processor, further cause the processor to receive a second input from the graphical user interface indicating a change in settings for the second lavatory and sending a third signal to the second control unit to adjust the second voltage of the second ion emitter in response to the second input, the second voltage being different than the first voltage.

In various embodiments, the second voltage is the same as the first voltage. In various embodiments, the instructions, when executed by the processor, further cause the processor to send a third signal to the first control unit to decrease the first voltage of the first ion emitter in response to a third input and send a fourth signal to the second control unit to increase the second voltage of the second ion emitter in response to the third input. In various embodiments, the first control unit is disposed in the first lavatory.

The foregoing features and elements may be combined in any combination, without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. While these exemplary embodiments are described in sufficient detail to enable those skilled in the art to practice the invention, it should be understood that other embodiments may be realized and that logical, chemical and mechanical changes may be made without departing from the spirit and scope of the invention. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Disclosed herein is lavatory including an integrated air ionizer. The air ionizer, in various embodiments, includes a control unit and one or more ion emitters. In various embodiments, the one or more ion emitters may be coupled to an air outlet located within the lavatory. In various embodiments the one or more ion emitters may be arranged perpendicular to a flow of air through the air outlet. In various embodiments, the one or more ion emitters may be located radially around the air outlet. In various embodiments, the one or more ion emitters are positioned to direct ions toward the passenger space within the lavatory. In various embodiments, the integrated air ionizer provides a high density of ions into the passenger area to combat chemicals and compounds that may cause malodor within the lavatory.

Figure 1:
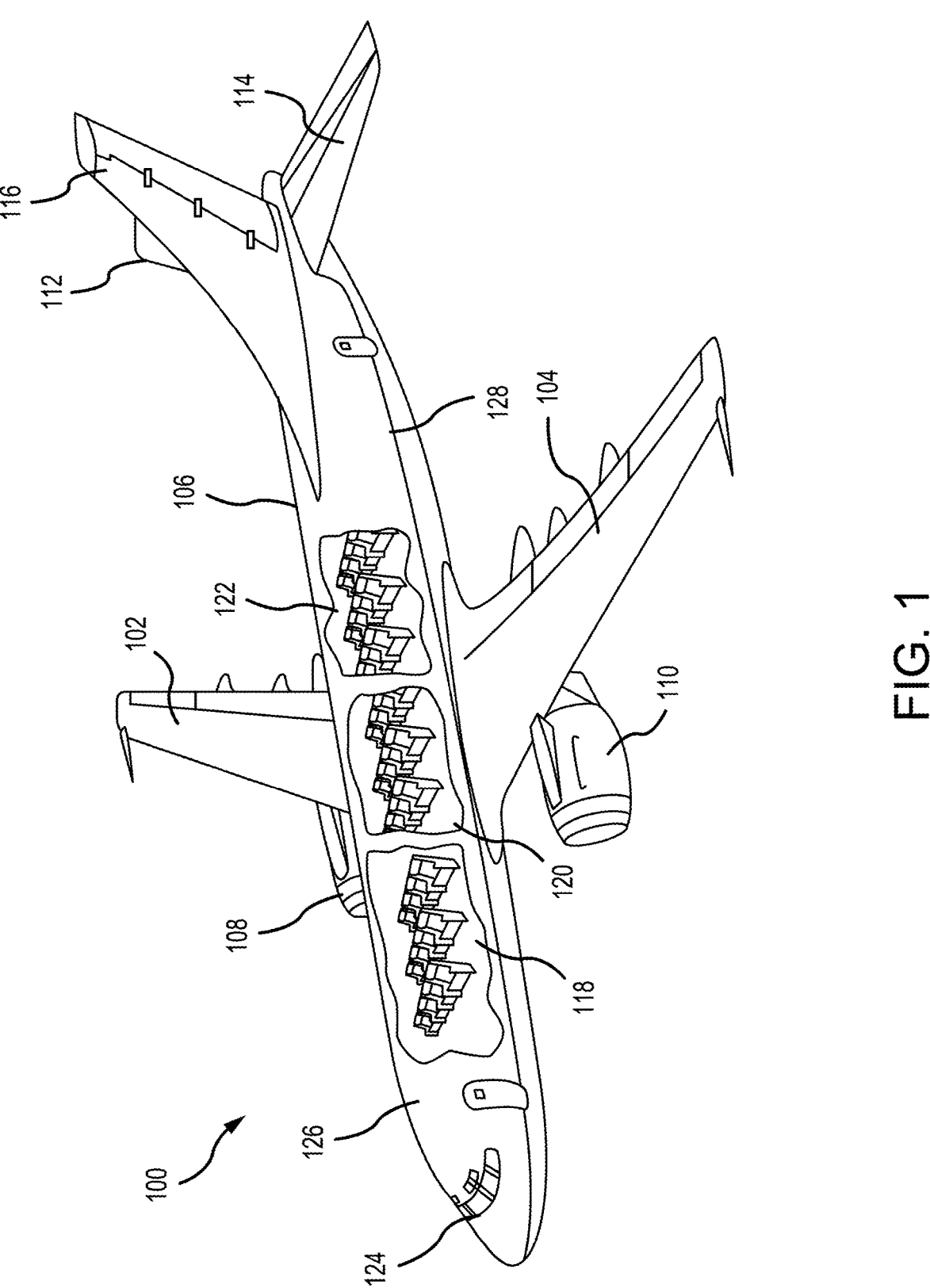
FIG. 1 illustrates an aircraft and various sections within the aircraft, in accordance with various embodiments.

Referring now to FIG. 1, an aircraft 100 and various sections within the aircraft is illustrated, in accordance with various embodiments. Aircraft 100 is an example of a passenger or transport vehicle in which smart air ionizers may be implemented in accordance with various embodiments. In various embodiments, aircraft 100 has a starboard wing 102 and a port wing 104 attached to a fuselage 106. In various embodiments, aircraft 100 also includes a starboard engine 108 connected to starboard wing 102 and a port engine 110 connected to port wing 104. In various embodiments, aircraft 100 also includes a starboard horizontal stabilizer 112, a port horizontal stabilizer 114, and a vertical stabilizer 116. In various embodiments, aircraft 100 also includes various cabin sections, including, for example, a first cabin section 118, a second cabin section 120, a third cabin section 122, and a pilot cabin 124. In various embodiments, aircraft 100 may include a front lavatory 126 and/or a rear lavatory 128.

Figure 2A:
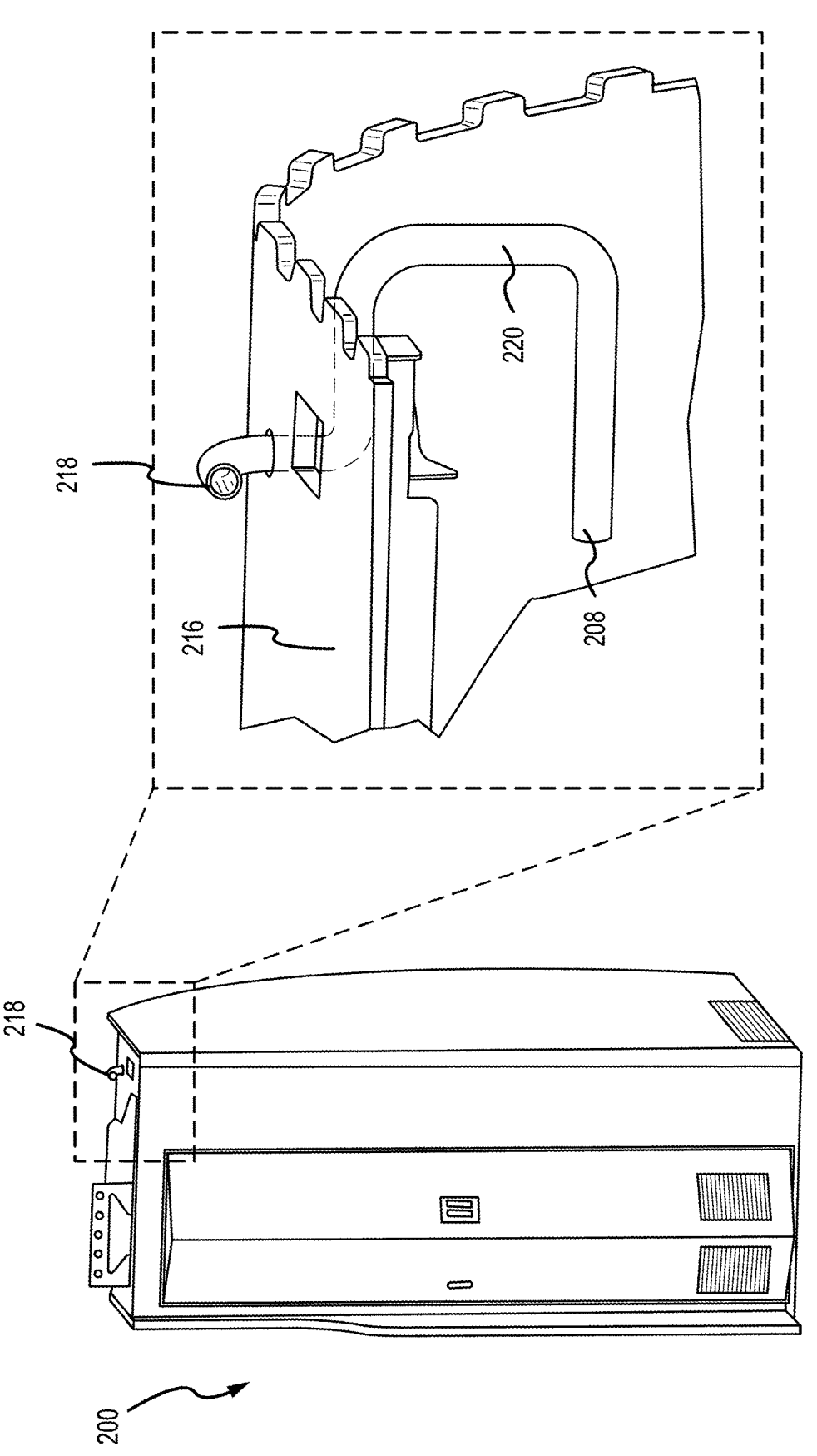
FIGS. 2A, 2B, and 2C illustrate a lavatory in an aircraft with an integrated air ionizer, in accordance with various embodiments.
Figure 2B:
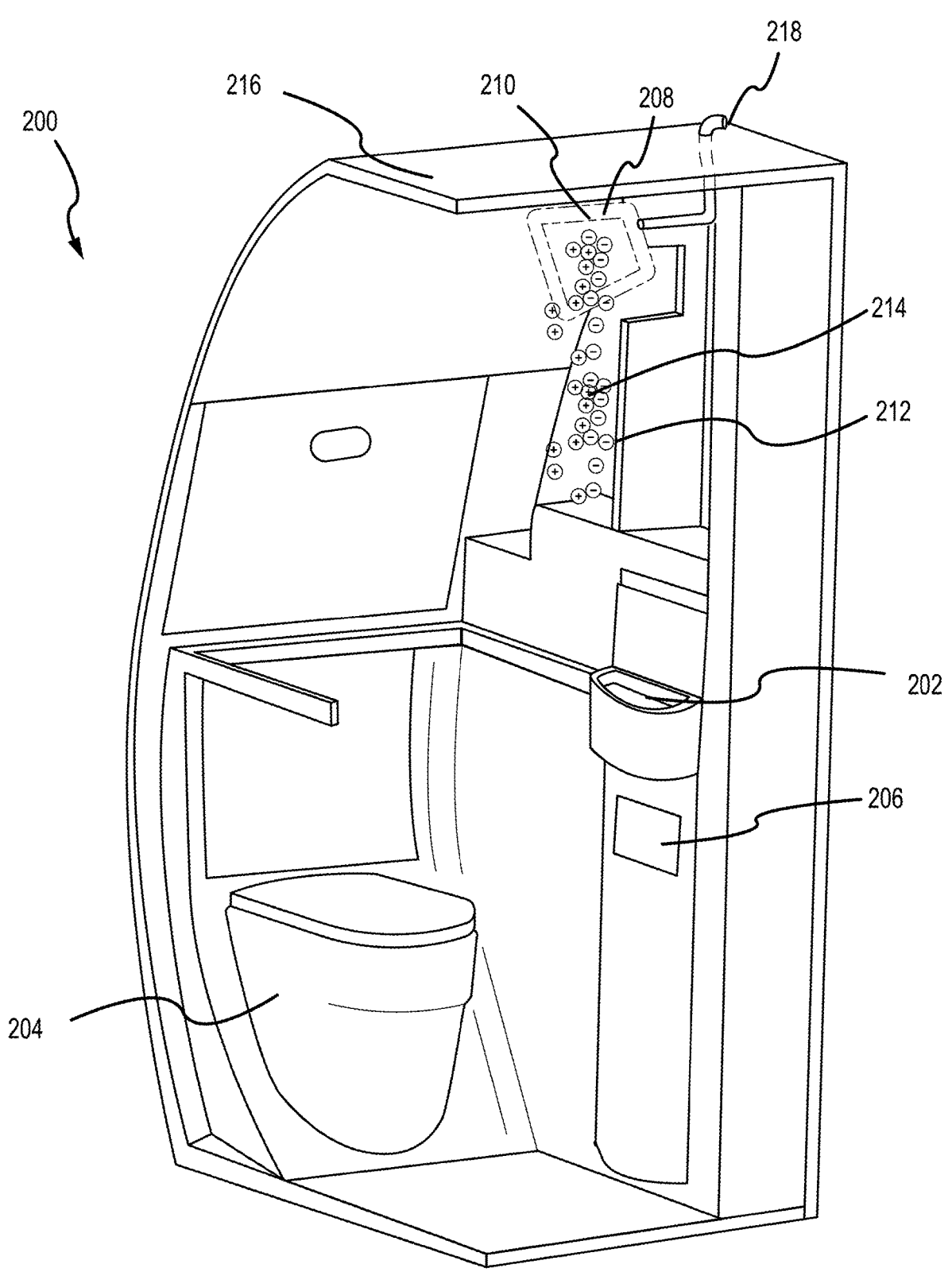
Figure 2C:
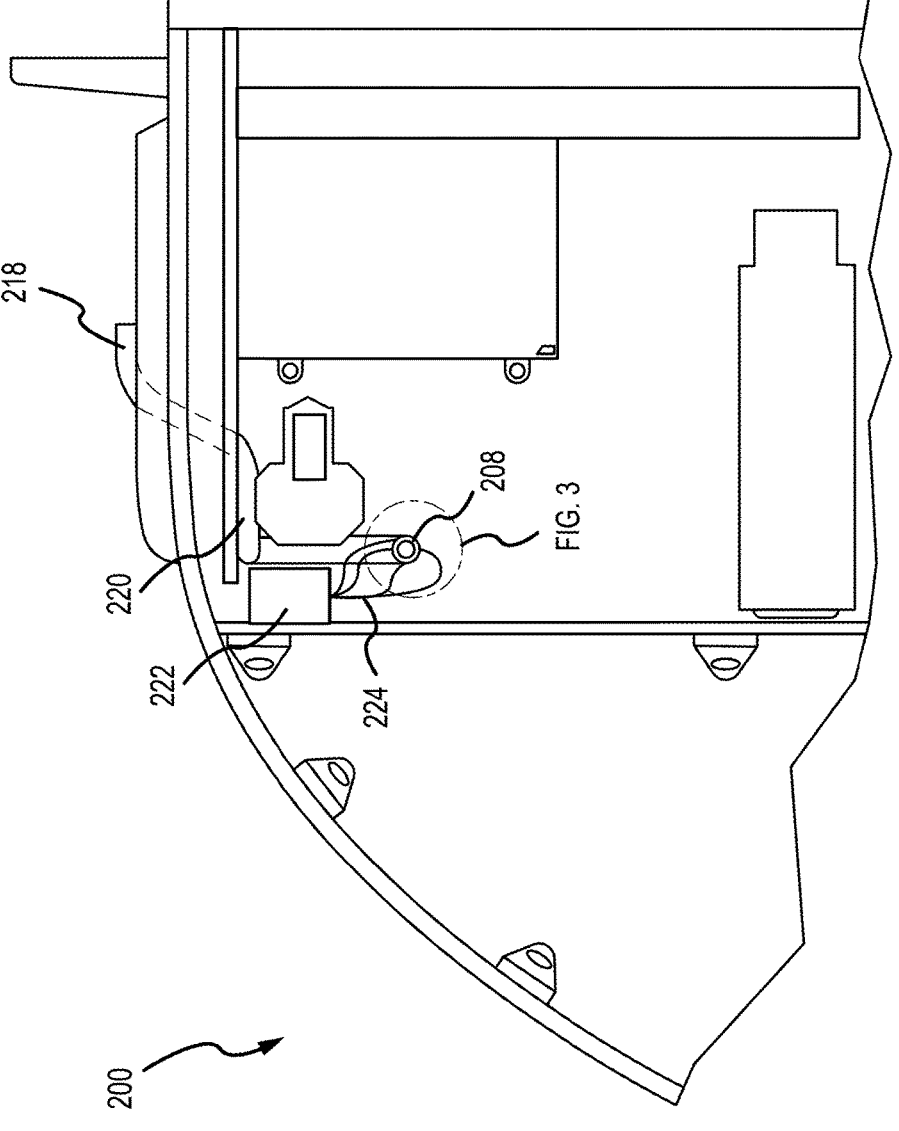

Referring now to FIGS. 2A-2C, a lavatory 200 is illustrated, in accordance with various embodiments. In various embodiments, lavatory 200 may be an example of front lavatory 126 or rear lavatory 128. FIG. 2A illustrates an exterior of lavatory 200. FIG. 2B illustrates an interior of lavatory 200. FIG. 2C illustrates the interior of lavatory 200 with the wall removed. Lavatory 200 may include a sink 202, a toilet 204, a trash receptacle 206, an air outlet 208, an ion emitter 210, a ceiling 216, an air inlet 218, and an air duct 220 coupled to air inlet 218 and air outlet 208. In various embodiments, ion emitter 210 may be mounted on ceiling 216 of lavatory 200, adjacent air outlet 208, within air outlet 208, or at an outlet of air outlet 208. In various embodiments, ion emitter 210 may be mounted within air outlet 208. ion emitter 210 generates ionized air particles, including negative ions 212 and positive ions 214, that are spread throughout lavatory 200 by air flow from air outlet 208.

In various embodiments, ion emitter 210, and more specifically, positive ions 214 may neutralize pathogens (e.g., bacteria, viruses, molds, dust, etc.) and/or malodor (i.e., unpleasant smells) that are airborne and on surfaces. Pathogens and malodor may be generated and/or spread by sink 202, toilet 204, and trash receptacle 206, among other locations. Pathogens and malodor may be airborne and/or settle on surfaces within lavatory 200, including sink 202, toilet 204, and trash receptacle 206, among others.

As illustrated in FIGS. 2A-2C, ion emitter 210 may be placed adjacent air outlet 208 so that ion emitter 210 ionizes the air exiting air outlet 208. Generally, ions created by ion emitter 210, such as negative ions 212 and positive ions 214, have an active life span of about 30 seconds to about 75 seconds, and more specifically, about 45 seconds to about 60 seconds. Accordingly, locating ion emitter 210 adjacent air outlet 208 improves the efficacy of negative ions 212 and positive ions 214 as compared to placing an air ionizer within ductwork of an air handling system or adjacent an air filter within the air handling system. In various embodiments, ion emitter 210 may be placed inside air outlet 208, and more specifically, within the ductwork behind air outlet 208 and immediately adjacent air outlet 208. In various embodiments, ion emitter 210 may be incorporated into air outlet 208 so the ion emitter 210 and air outlet 208 operate as a single unit to ionize and disperse air throughout lavatory 200.

Lavatory 200 further includes a control unit 222 that is operatively and electrically coupled to ion emitters 210 by one or more wires 224. Control unit 222 controls each ion emitter 210 by adjusting a voltage, a current, a timing, and/or other parameters to increase or decrease a number of ions produced by each ion emitters 210. In various embodiments, increasing a voltage and/or a current to each ion emitters 210 increases the number of ions produced by ion emitters 210. In various embodiments, decreasing the voltage and/or the current to each ion emitters 210 decreases the number of ions produced by ion emitter 210. In various embodiments, control unit 308 may control each ion emitters 210 individually and/or as all together. In various embodiments, control unit 222 may step up a received alternating current (AC) or a direct current (DC) voltage to a high voltage for use by ion emitter 210. In various embodiments, control unit 222 may be connected to a 115 V AC power source. In various embodiments, control unit 222 may be connected to a 28 V DC power source. In various embodiments, control unit 222 may output about 2.5 KV to about 12.5 KV, and more specifically, about 5 KV to about 10 KV.

Control unit 222 may comprise one or more processors configured to implement various logical operations in response to execution of instructions, for example, instructions stored on a non-transitory, tangible, computer-readable medium. The one or more processors can be a general purpose processor, a microprocessor, a microcontroller, a digital signal processor (DSP), an application specific integrated circuit (ASIC), a field programmable gate array (FPGA) or other programmable logic device, discrete or transistor logic, discrete hardware components, or any combination thereof.

Control unit 222 may further comprise memory to store data, executable instructions, system program instructions, and/or controller instructions to implement the control logic of control unit 222.

Figure 3C:
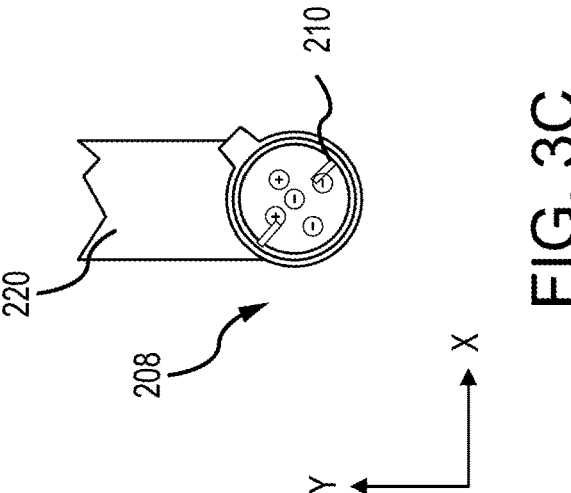
FIGS. 3A, 3B, and 3C illustrate ion emitters installed on an air outlet within a lavatory with an integrated air ionizer, in accordance with various embodiments.
Figure 3B:
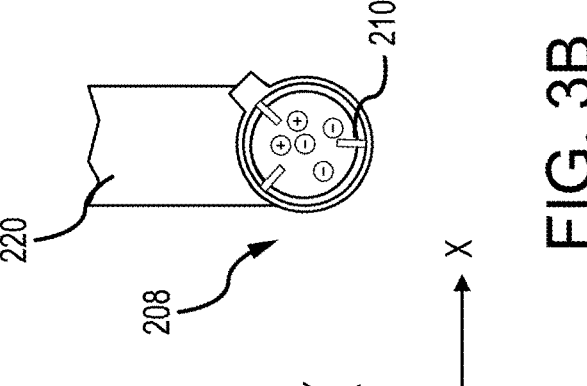
Figure 3A:
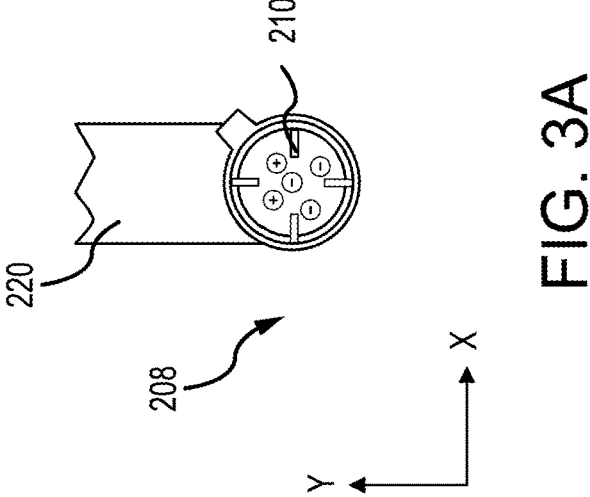

Referring now to FIGS. 3A-3C, ion emitter arrangements around air outlet 208 are illustrated, in accordance with various embodiments. FIG. 3A includes four ion emitters 210 disposed radially around an inner diameter of air outlet 208. In various embodiments, each of the four ion emitters 210 may extend orthogonal to the inner diameter of air outlet 208 so that each ion emitter 210 extends perpendicular to the air flow exiting air outlet 208. In various embodiments, each ion emitter 210 may extend inward from the inner diameter at different angles. In various embodiments, ion emitters 210 may be positioned equidistant from each other, as illustrated in FIG. 3A. In various embodiments, the spacing between ion emitters 210 may be non-uniform.

FIG. 3B illustrates three ion emitters 210 disposed radially around an inner diameter of air outlet 208. In various embodiments, each of the three ion emitters 210 may extend orthogonal to the inner diameter of air outlet 208 so that each ion emitter 210 extends perpendicular to the air flow exiting air outlet 208. In various embodiments, each ion emitter 210 may extend inward from the inner diameter at different angles. In various embodiments, each of the three ion emitters 210 may be positioned equidistant from each other. In various embodiments, the spacing between one or more of ion emitters 210 may be non-uniform.

FIG. 3C illustrates two ion emitters 210 disposed radially around an inner diameter of air outlet 208. In various embodiments, both ion emitters 210 may extend orthogonal to the inner diameter of air outlet 208 so that each ion emitter 210 extends perpendicular to the air flow exiting air outlet 208. In various embodiments, each ion emitter 210 may extend inward from the inner diameter at different angles. In various embodiments, both ion emitters 210 may be positioned equidistant from each other. In various embodiments, the spacing between ion emitters 210 may be non-uniform.

Figure 4:
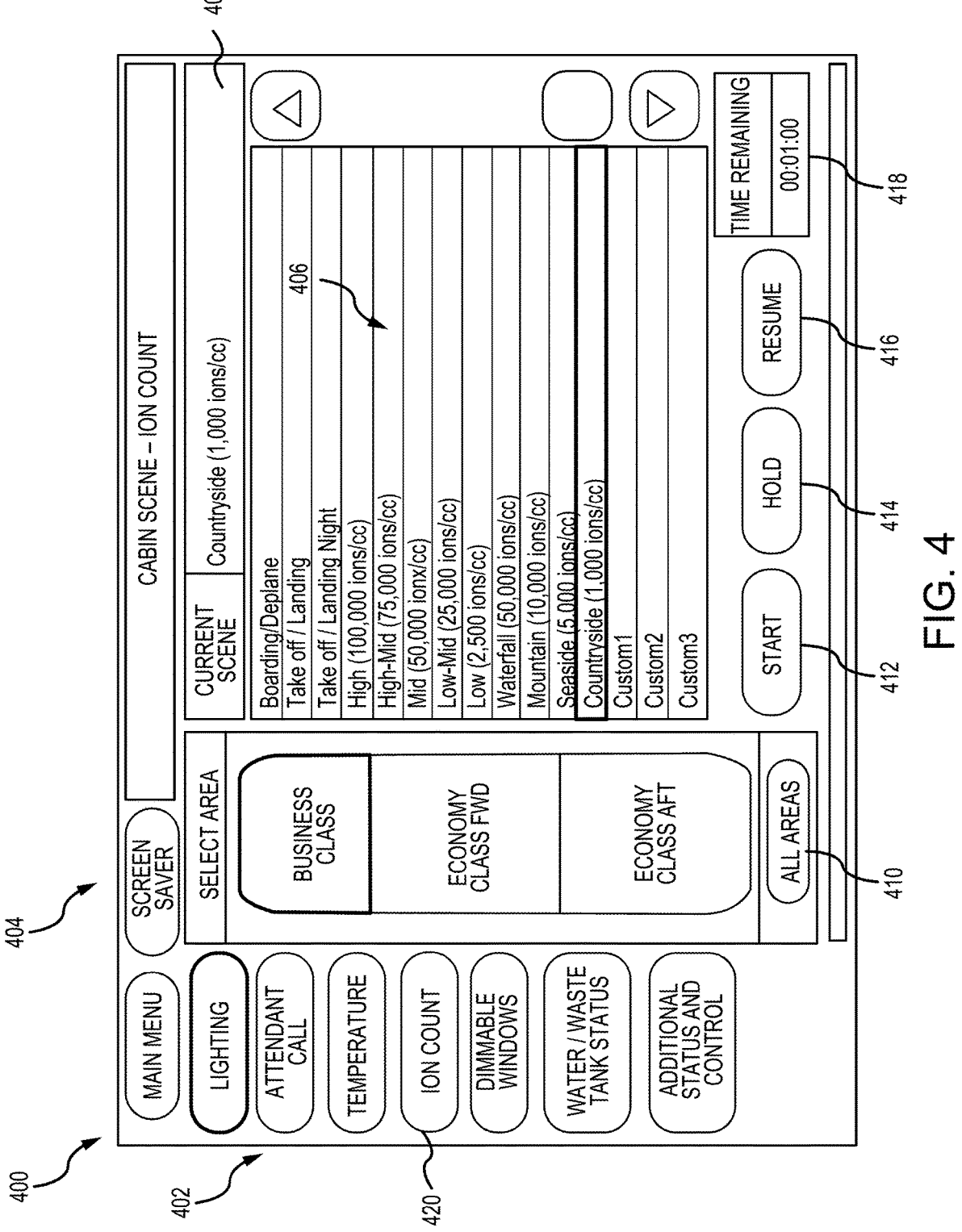
FIG. 4 illustrates a user interface for controlling an air ionizer in a lavatory, in accordance with various embodiments.

Referring now to FIG. 4, a graphical user interface, GUI 400, for controlling one or more air ionizers is illustrated, in accordance with various embodiments. In various embodiments, GUI 400 may communicate with control unit 308. In various embodiments, the one or more air ionizers may be examples of ion emitters 210 described above in FIG. 2. In various embodiments, the one or more air ionizers may be examples of ion emitter 310 described above in FIG. 3. It should be appreciated that GUI 400 as described below is not intended to be limiting, but to be exemplary one implementation of a user interface for controlling one or more air ionizers and is for case of discussion. As such, GUI 400 may be presented differently and/or provide more or less functionality than what is discussed below.

GUI 400 includes an options menu 402, a cabin area selector 404, a scene selector 406, a current scene indicator 408, an all areas button 410, a start button 412, a hold button 414, a resume button 416, and a timer 418. Options menu 402 provides a crew member the ability to control different aspects of the cabin including lighting, temperature, windows, and ion count and to view status of the cabin including attendant call button and water status. Cabin area selector 404 allow the crew member to select which cabin section to monitor such as business class, economy class forward, and economy class aft. Pressing all areas button 410 may select all cabin areas for adjustment.

Selecting ion count 420 presents the crew member with scene selector 406 and current scene indicator 408. In various embodiments, scene selector 406 may present the crew member with different scenes to adjust the number of ions being generated by air ionizers and ion emitters (e.g., ion emitter 210) within each cabin area. As illustrated, scene selector 406 presents the cabin crew with different options such as "Boarding/Deplane", "Take off/Landing", "Take off/Landing Night", "High", "High-Mid", "Mid", "Mid-Low", "Low", "Waterfall", "Mountain", "Seaside", "Countryside", "Custom1", "Custom2", and "Custom3". The selections in scene selector 406 are intended to simplify the control of the air ionizers for the cabin crew. As illustrated, the different scenes may produce different numbers of ions depending on the current state of the cabin area. For example, the cabin crew may select "Countryside" or "Low" in response to normal conditions within the cabin area. The cabin crew may select "High" or "Waterfall" in response to a malodor within the cabin area (e.g., a soiled diaper, garbage, lavatory, etc.). Doing so provides the cabin crew the ability to adjust the number of ions per cubic centimeter (ions/cc) per unit time to a level that is comfortable for the passengers by increasing or decreasing the voltage supplied to each ion emitter (e.g., ion emitter 210).

Start button 412 may change the selected scene. Hold button 414 may pause the selected scene for a time. Resume button 416 may resume the selected scene after being on hold. Timer 418 may provide an indication of how long the selected scene has been running or on hold. In various embodiments, GUI 400 may be used to control ion output in each lavatory independently from other lavatories. That is, a first scene may be selected for a first lavatory and a second scene may be selected for a second lavatory. This allows for individual control of the different lavatories based on the use of each lavatory.

Figure 5:
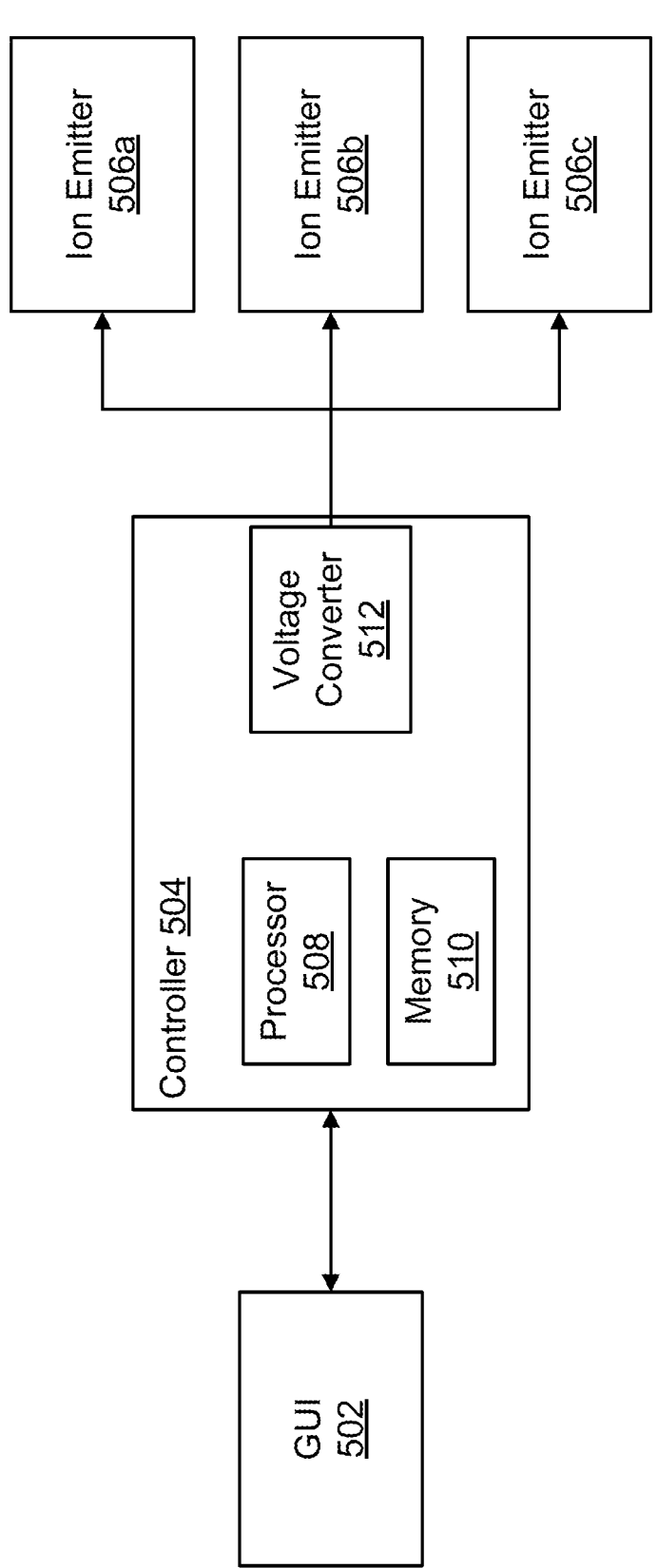
FIG. 5 illustrates a system for controlling an air ionizer in a lavatory, in accordance with various embodiments.

Referring now to FIG. 5, a system 500 for controlling one or more air ionizers is illustrated, in accordance with various embodiments. System 500 includes a graphical user interface (GUI) 502, a controller 504, and ion emitters 506a-506c. In various embodiments, GUI 502 may be an example of GUI 400 described above in FIG. 4. In various embodiments, controller 504 may be an example of control unit 222 described above in FIG. 2B. In various embodiments, controller 504 may be an example of a central aircraft controller or other server. In various embodiments, ion emitters 506a-506c may be examples of ion emitter 310 described in FIGS. 3A-3C. In various embodiments, ion emitters 506a-506c may be examples of ion emitter 210 described above in FIG. 2.

Controller 504 includes a processor 508, a memory 510, and a voltage converter 512. Processor 508 is configured to communicate with GUI 502 to receive commands from a crew member and to control ion emitters 506a-506c in response to the received commands. Memory 510 is configured to store data from GUI 502 and processor 508. Voltage converter 512 is configured to receive commands from processor 508 and convert an input voltage (e.g., 28 VDC, 115 VAC) to a high voltage output (e.g., 10 kV DC) for use by ion emitters 506a-506c).

Processor 508 may comprise one or more processors configured to implement various logical operations in response to execution of instructions, for example, instructions stored on a non-transitory, tangible, computer-readable medium. The one or more processors can be a general purpose processor, a microprocessor, a microcontroller, a digital signal processor (DSP), an application specific integrated circuit (ASIC), a field programmable gate array (FPGA) or other programmable logic device, discrete or transistor logic, discrete hardware components, or any combination thereof. Memory 510 may comprise memory to store data, executable instructions, system program instructions, and/or controller instructions to implement the control logic of processor 508.

System program instructions and/or controller instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 5% of a stated value. Additionally, the terms "substantially," "about" or "approximately" as used herein represent an amount close to the stated amount that still performs a desired function or achieves a desired result. For example, the term "substantially," "about" or "approximately" may refer to an amount that is within 5% of a stated amount or value.

Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above-described concepts can be used alone or in combination with any or all of the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. An aircraft lavatory, comprising:
an air duct including an air inlet and an air outlet, the air outlet extending into an interior of the aircraft lavatory;
a plurality of ion emitters disposed radially around an inner diameter of the air outlet, wherein each ion emitter of the plurality of ion emitters extends orthogonal to an inner diameter of the air outlet so that each ion emitter extends perpendicular to the air flow exiting the air outlet and wherein each ion emitter of the plurality of ion emitters extends inward from the inner diameter at a different angle from one another; and
a control unit electronically coupled to the plurality of emitters, the control unit configured to control an ion output of each ion emitter of the plurality of ion emitters.

2. The aircraft lavatory of claim 1, wherein the ion emitter is configured to be in an air flow passing through the air outlet.

3. The aircraft lavatory of claim 1, wherein the air inlet extends to an exterior of the aircraft lavatory to provide the air duct with air from outside of the aircraft lavatory.

4. The aircraft lavatory of claim 1, wherein the control unit comprises:
a voltage input having a first voltage; and
a voltage output having a second voltage that is greater than the first voltage, the voltage output being coupled to each ion emitter of the plurality of ion emitters.

5. An aircraft, comprising:
a lavatory including an interior and an exterior;
an air duct extending from the exterior of the lavatory to the interior of the lavatory, the air duct including an air outlet disposed within the interior of the lavatory;
a plurality of ion emitters disposed radially around an inner diameter of the air outlet, wherein each ion emitter of the plurality of ion emitters extends orthogonal to an inner diameter of the air outlet so that each ion emitter extends perpendicular to the air flow exiting the air outlet and wherein each ion emitter of the plurality of ion emitters extends inward from the inner diameter at a different angle from one another; and
a control unit electronically coupled to the ion emitter, the control unit configured to control an ion generation of the ion emitter.

6. The aircraft of claim 5, wherein the ion emitter is configured to be in an air flow passing through the air outlet and into the interior of the lavatory.

7. The aircraft of claim 5, wherein the lavatory further includes an interior wall disposed between the control unit and the interior of the lavatory.

8. The aircraft of claim 5, wherein the control unit comprises:
a voltage input having a first voltage; and
a voltage output having a second voltage that is greater than the first voltage, the voltage output being coupled to each ion emitter of the plurality of ion emitters.

9. A system, comprising:
a first ion emitter coupled to a first air outlet inside a first lavatory;
a first control unit electronically coupled to the first ion emitter;
a second ion emitter coupled to a second air outlet inside a second lavatory;
a second control unit electronically coupled to the second ion emitter,
a graphical user interface;
a processor electronically coupled to the first control unit; and
a memory operatively coupled to the processor, the memory comprising instructions stored thereon that, when executed by the processor, cause the processor to:
receive a first input from the graphical user interface; and
send a first signal to the first control unit to adjust a first voltage to the first ion emitter in response to the input;
receive a second input from the graphical user interface indicating a change in settings for the second lavatory; and
send a second signal to the second control unit to adjust a second voltage of the second ion emitter in response to the second input.

10. The system of claim 9, wherein the second voltage is different than the first voltage.

11. The system of claim 9, wherein the second voltage is the same as the first voltage.

12. The system of claim 9, wherein the instructions, when executed by the processor, further cause the processor to:
send a third signal to the first control unit to decrease the first voltage of the first ion emitter in response to a third input; and
send a fourth signal to the second control unit to increase the second voltage of the second ion emitter in response to the third input.

13. The system of claim 9, wherein the first control unit is disposed in the first lavatory.

* * * * *